(12) United States Patent
Murtaza et al.

(10) Patent No.: US 12,043,856 B2
(45) Date of Patent: Jul. 23, 2024

(54) MOLECULAR TAGGING METHODS AND SEQUENCING LIBRARIES

(71) Applicant: THE TRANSLATIONAL GENOMICS RESEARCH INSTITUTE, Phoenix, AZ (US)

(72) Inventors: Muhammed Murtaza, Phoenix, AZ (US); Maria de las Nieves Perdigones Borderias, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 675 days.

(21) Appl. No.: 16/302,568

(22) PCT Filed: May 24, 2017

(86) PCT No.: PCT/US2017/034329
§ 371 (c)(1),
(2) Date: Nov. 16, 2018

(87) PCT Pub. No.: WO2017/205540
PCT Pub. Date: Nov. 30, 2017

(65) Prior Publication Data
US 2019/0292575 A1  Sep. 26, 2019

Related U.S. Application Data

(60) Provisional application No. 62/340,954, filed on May 24, 2016.

(51) Int. Cl.
*C12P 19/34* (2006.01)
*C12N 15/66* (2006.01)
(Continued)

(52) U.S. Cl.
CPC .............. *C12P 19/34* (2013.01); *C12N 15/66* (2013.01); *C12Q 1/68* (2013.01); *C12Q 1/6806* (2013.01);
(Continued)

(58) Field of Classification Search
CPC ........... C12P 19/34; C12N 15/66; C12Q 1/68; C12Q 1/6806; C12Q 1/6853; C12Q 1/686;
(Continued)

(56) References Cited

U.S. PATENT DOCUMENTS 9,970,024 B2 * 3/2018 Church et al. ......... C12N 15/85
2004/0101886 A1 * 5/2004 Bowdish et al. ................. 435/6
(Continued)

FOREIGN PATENT DOCUMENTS

WO  2007/018601 A1   2/2007
WO  2009/091719 A1   7/2009
(Continued)

OTHER PUBLICATIONS

Grothues et al. "PCR amplification of megabase DNA with tagged random primers (T-PCR)" Nucleic Acids Res. 1993, 21(5):1321-1322). (Year: 1993).*
(Continued)

*Primary Examiner* — Kaijiang Zhang
(74) *Attorney, Agent, or Firm* — Casimir Jones, S.C.; J. Mitchell Jones (57) ABSTRACT

The invention provides a tagged sequencing library and methods for tagging low abundance target sequences and generating a sequencing library for detecting low abundance target sequences.

21 Claims, 7 Drawing Sheets

Specification includes a Sequence Listing.

(51) Int. Cl.
    *C12Q 1/68*         (2018.01)
    *C12Q 1/6806*     (2018.01)
    *C12Q 1/6853*     (2018.01)
    *C12Q 1/686*      (2018.01)
    *C40B 40/06*      (2006.01)

(52) U.S. Cl.
    CPC ........... *C12Q 1/6853* (2013.01); *C12Q 1/686* (2013.01); *C40B 40/06* (2013.01); *C12Q 2525/191* (2013.01); *C12Q 2600/16* (2013.01)

(58) Field of Classification Search
    CPC .......... C12Q 2525/191; C12Q 2600/16; C40B 40/06
    See application file for complete search history.

(56) References Cited

U.S. PATENT DOCUMENTS

| | | | |
|---|---|---|---|
| 2007/0020640 A1* | 1/2007 | McCloskey et al. | 435/6 |
| 2011/0269124 A1* | 11/2011 | Stephens | 435/6 |
| 2012/0220494 A1* | 2/2012 | Samuels et al. | 506/16 |
| 2014/0004520 A1 | 1/2014 | Mohapatra et al. | |
| 2014/0193860 A1* | 7/2014 | Bevilacqua et al. | C12P 19/34 |
| 2015/0031042 A1 | 1/2015 | Wood et al. | |
| 2016/0340746 A1* | 11/2016 | Makarov et al. | C12Q 1/68 |
| 2017/0037459 A1* | 2/2017 | Godwin | C12Q 1/6853 |
| 2017/0206310 A1* | 7/2017 | Ishii et al. | G06F 19/18 |
| 2018/0051277 A1* | 2/2018 | Godfrey et al. | C12N 15/1065 |

FOREIGN PATENT DOCUMENTS

| | | |
|---|---|---|
| WO | 2014/071361 A1 | 5/2014 |
| WO | 2016/025796 A1 | 2/2016 |

OTHER PUBLICATIONS

Liu et al. "Rolling Circle DNA Synthesis: Small Circular Oligonucleotides as Efficient Templates for DNA Polymerases" J Am Chem Soc. Feb. 21, 1996; 118(7): 1587-1594. doi:10.1021/ja952786k (Year: 1996).*

Cibulskis, K., et al., Sensitive detection of somatic point mutations in impure and heterogeneous cancer samples. Nat Biotechnol 2013; 31(3): 213-219.

Christoforides, A., et al., Identification of somatic mutations in cancer through Bayesian-based analysis of sequenced genome pairs. BMC Genomics 2013; 14:302.

Saunders, C. T., et al., Strelka: accurate somatic small-variant calling from sequenced tumor-normal sample pairs. Bioinformatics 2012; 28(14):1811-1817.

McGranahan, N., et al., Clonal status of actionable driver events and the timing of mutational processes in cancer evolution. Sci Transl Med 2015; 7(283):283ra54.

Roth, A., et al., PyClone: statistical inference of clonal population structure in cancer. Nat Methods 2014; 11 (4):396-398.

Kwok, C. K., et al. A hybridization-based approach for quantitative and low-bias single-stranded DNA ligation. Anal Biochem 2013; 435(2):181-186.

Murtaza, M., et al. Multifocal clonal evolution characterized using circulating tumour DNA in a case of metastatic breast cancer. Nat Commun 2015; 6:8760.

Smith, T., et al. UMI-tools: modeling sequencing errors in Unique Molecular Identifiers to improve quantification accuracy. Genome Res 2017; 27:491-499.

Katz, S. J., et al. Reducing Overtreatment of Cancer With Precision Medicine: Just What the Doctor Ordered. JAMA 2018; 319:1091-1092.

Chaudhuri, A. A., et al. Early Detection of Molecular Residual Disease in Localized Lung Cancer by Circulating Tumor DNA Profiling. Cancer Discov 2017; 7(12):1394-1403.

Garcia-Murillas, I., et al. Mutation tracking in circulating tumor DNA predicts relapse in early breast cancer. Sci Transl Med 2015; 7(302):302ra133.

Tie, J., et al. Circulating tumor DNA analysis detects minimal residual disease and predicts recurrence in patients with stage II colon cancer. Sci Transl Med 2016; 8(346):346ra92.

Abbosh, C., et al. Phylogenetic ctDNA analysis depicts early-stage lung cancer evolution. Nature 2017; 545 (7655):446-451.

Forshew, T., et al. Noninvasive identification and monitoring of cancer mutations by targeted deep sequencing of plasma DNA. Sci Transl Med 2012; 4(136):136ra68.

Kinde, I., et al. Detection and quantification of rare mutations with massively parallel sequencing. Proc Natl Acad Sci U S A 2011; 108(23):9530-9535.

Markus, H., et al. Evaluation of pre-analytical factors affecting plasma DNA analysis. Sci Rep 2018; 8(1):7375.

Cortazar, P., et al. Meta-analysis results from the collaborative trials in neoadjuvant breast cancer (CTNeoBC). Abstracts: Thirty-Fifth Annual CTRC-AACR San Antonio Breast Cancer Symposium— Dec. 4-8, 2012; San Antonio, TX; Cancer Res 2012; 72(24 Suppl):Abstract nr S1-S11.

Symmans, W. F., et al. Long-Term Prognostic Risk After Neoadjuvant Chemotherapy Associated With Residual Cancer Burden and Breast Cancer Subtype. J Clin Oncol 2017; 35(10):1049-1060.

Chagpar, A. B., et al. Accuracy of physical examination, ultrasonography, and mammography in predicting residual pathologic tumor size in patients treated with neoadjuvant chemotherapy. Annals of Surgery 2006; 243(2):257-264.

Yuan, Y., et al. Accuracy of MRI in prediction of pathologic complete remission in breast cancer after preoperative therapy: a meta-analysis. AJR Am J Roentgenol 2010; 195(1);260-268.

Zviran, A., et al. Genome-wide cell-free DNA mutation integration for sensitive cancer detection. In: Proceedings of the American Association for Cancer Research Annual Meeting 2018; Apr. 14-18, 2018; Chicago, IL. Philadelphia (PA): AACR; Cancer Res 2018;78(13 Suppl):Abstract nr 3247.

Ruiz-Valdepenas, A., et al. MA 11.02 Circulating Tumor DNA in Early Stage NSCLC: High Sensitivity Analysis in Low Burden Disease. Lucid Study Update. Journal of Thoracic Oncology 2017; 12(11):S1843-S1844.

Newman, A. M., et al. Integrated digital error suppression for improved detection of circulating tumor DNA. Nat Biotechnol 2016; 34(5):547-555.

Bettegowda, C., et al. Detection of circulating tumor DNA in early- and late-stage human malignancies. Sci Transl Med 2014; 6(224):224ra24.

Cohen, J. D., et al. Detection and localization of surgically resectable cancers with a multi-analyte blood test. Science 2018; 359(6378):926-930.

Sparano, J. A., et al. Adjuvant Chemotherapy Guided by a 21-Gene Expression Assay in Breast Cancer. N Engl J Med 2018; 379(2):111-121.

Tie, J., et al. Serial circulating tumour DNA analysis during multimodality treatment of locally advanced rectal cancer: a prospective biomarker study. Gut 2019; 68(4):663-671.

Riva, F., et al. Patient-Specific Circulating Tumor DNA Detection during Neoadjuvant Chemotherapy in Triple-Negative Breast Cancer. Clin Chem 2017; 63(3):691-699.

Li, H. Aligning sequence reads, clone sequences and assembly contigs with BWA-MEM. arXiv preprint 2013; arXiv:1303.3997.

Van Der Auwera, G. A., et al. From FastQ data to high confidence variant calls: the Genome Analysis Toolkit best practices pipeline. Curr Protoc Bioinformatics 2013; 43:11.10.1-33.

Garrison, E., et al. Halotype-based variant detection from short-read sequencing. ArXiv e-prings 2012; arXiv:1207.3907.

Favero, F., et al. Sequenza: allele-specific copy number and mutation profiles from tumor sequencing data. Ann Oncol 2015; 26(1):64-70.

Pereira, B., et al. The somatic mutation profiles of 2,433 breast cancer refines their genomic and transcriptomic landscapes. Nat Commun 2016; 7:11479.

Untergasser, A., et al. Primer3—new capabilities and interfaces. Nucleic Acids Res 2012; 40(15):e115.

(56) References Cited

OTHER PUBLICATIONS

Kielbasa, S. M., et al. Adaptive seeds tame genomic sequence comparison. Genome Res 2011; 21(3):487-493.

Mikhail V Pogrelyy et al. "Persisting fetal clonotypes influence the structure and overlap of adult human T cell receptor repertoires" ariv.org, Cornell University Library, 201 Olin Library Cornell University Ithaca, NY 14853, Feb. 9, 2016, 21 Pages.

Zhou Shuntai et al. "Primer ID Validates Template Sampling Depth and Greatly Reduces the Error Rate of Next-Generation Sequencing of HIV-1 Genomic RNA Populations" Journal of Virology (Online), American Society for Microbiology, vol. 89, No. 16, Aug. 15, 2015, pp. 8540-8555.

\* cited by examiner

MOLECULAR TAGGING METHODS AND SEQUENCING LIBRARIES

RELATED APPLICATION DATA

This application is the U.S. National Stage of International Application No. PCT/US2017/034329, filed on May 24, 2017, which claims priority to and the benefit of U.S. Provisional Application No. 62/340,954, filed on May 24, 2016, the contents of each of which are hereby incorporated by reference in their entireties.

REFERENCE TO SEQUENCE LISTING SUBMITTED ELECTRONICALLY

A sequence listing is submitted electronically via EFS-Web as an ASCII-formatted sequence listing with a file named "91482_216_sub_seq_list" created on Jun. 19, 2017, and having a size of 2 kilobytes, and is filed concurrently with the specification. The sequence listing contained in this ASCII-formatted document is part of the specification and is herein incorporated by reference in its entirety.

FIELD OF THE INVENTION

The present invention is related to methods of molecular tagging of nucleic acids, for example, for the preparation of sequencing libraries. The invention is also directed to tagged sequencing libraries.

BACKGROUND OF THE INVENTION

Molecular barcoding or tagging involves attaching a unique or degenerate oligonucleotide label to each template molecule in the first or early steps of sequencing library preparation so that any low abundance signals of variant may be distinguished from noise introduced during the process. The process has recently been described as a viable approach for detection and quantification of low abundance variants in complex mixture of nucleic acids. The overall goal is to improve sensitivity and accuracy of next generation sequencing for identifying, detecting, and quantifying nucleic acid molecules of any given type (or carrying a variant). However, existing methods are still incapable of tagging target sequences that are of low abundance. Most current methods have limited efficiency in capture molecules and require high amount of input molecules to achieve adequate sensitivity and accuracy. These obstacles are particularly problematic in the early detection of cancer or monitoring in patients with early stage cancers. In a normal individual, only 3,000 to 5,000 copies of the genome are found in one milliliter of plasma. Within that, the occurrences of a copy of the genome containing a cancer mutation can be as low as 1 in 10,000 copies of the wild-type genome. In combination with the distortion factors from PCR and sequencing, early detection of a cancer-causing mutation is trying to find the proverbial needle in a hay farm rather than a single haystack. Accordingly, there is a need for improving identification and detection of low abundance variants in the genome.

SUMMARY OF THE INVENTION

The invention is directed to methods of adding oligonucleotide tags to a nucleic acid sequence and of producing a sequencing library and directed to a sequencing library comprising nucleic acid sequences tagged with an adapter oligonucleotide at the 3'-end.

The methods of adding oligonucleotide tags to a nucleic acid sequence in a sample comprise ligating an adapter oligonucleotide to the 3'-end of the nucleic acid sequence, wherein the adapter oligonucleotide comprises a stem-loop intramolecular nucleotide base pairing, a hydroxyl group at the 3'-end, a phosphate at the 5'-end, a random region complementary to nucleic acid sequence, and a random region in the loop comprising the molecular barcode.

The methods of producing a sequencing library comprise ligating an adapter oligonucleotide to the 3'-end of the nucleic acid sequence to produce a hybrid sequence comprising the sequence of interest on the nucleic acid sequence and the adapter oligonucleotide, wherein the adapter oligonucleotide comprises: a stem-loop intramolecular nucleotide base pairing, a hydroxyl group at the 3'-end, a phosphate at the 5'-end, a random region complementary to nucleic acid sequence, and a random region in the loop comprising the molecular barcode; and amplifying hybrid sequence with a first set of primers. In some implementations, the first set of primers comprises a forward universal primer and a reverse universal sample barcoding primer, wherein the reverse universal sample barcoding primer comprises a sample barcode. In these implementations, amplifying hybrid sequence with the first set of primers produces a barcoded sequence. In other implementations, the first set of primers comprises a target specific primer and a reverse universal primer. In these implementations, amplifying hybrid sequence with the first set of primers produces a target specific sequence, and the methods further comprise amplifying the target specific sequence with a second set of primers comprising a forward universal primer and sample barcoding primer to produce a barcoded sequence. In some aspects, the methods further comprises amplifying the target-specific sequence with a nested target specific primer and the universal primer prior to amplification with the second set of primers.

In some embodiments, the methods of the invention comprise a pre-amplification step to increase the sample number. Thus, prior to the ligation step, the methods comprise annealing a first universal primer to the nucleic acid sequence in the sample, wherein the first universal primer is complementary to a sequence of interest on the nucleic acid sequence and then linearly amplifying the nucleic acid sequence.

In some aspects, the nucleic acid in the sample is fractionated. In some implementations, the methods comprise cleaning up after each amplification step with exonuclease and alkaline phosphatase.

In other aspects, the invention relates to a method of adding oligonucleotide tags to a nucleic acid sequence in a sample, the method comprising the steps of: annealing a first universal primer to the nucleic acid sequence in the sample, wherein the first universal primer is complementary to a sequence of interest on the nucleic acid sequence; linearly amplifying the nucleic acid sequence; and ligating an adapter oligonucleotide to the 3'-end of the nucleic acid sequence, wherein the adapter oligonucleotide comprises: a stem-loop intramolecular nucleotide base pairing; a hydroxyl group at the 3'-end; a phosphate at the 5'-end; a random region complementary to the nucleic acid sequence; and a random region in the loop comprising a molecular barcode.

In yet other aspects, the invention relates to a method of producing a sequencing library, the method comprising the steps of: annealing a first universal primer to the nucleic acid sequence in the sample, wherein the first universal primer is complementary to a sequence of interest on the nucleic acid sequence; linearly amplifying the nucleic acid sequence; ligating an adapter oligonucleotide to the 3'-end of the nucleic acid sequence to produce a hybrid sequence comprising the sequence of interest on the nucleic acid sequence and the adapter oligonucleotide, wherein the adapter oligonucleotide comprises: a stem-loop intramolecular nucleotide base pairing; a hydroxyl group at the 3'-end; a phosphate at the 5'-end; a random region complementary to the nucleic acid sequence; and a random region in the loop comprising a molecular barcode; and amplifying hybrid sequence with a first set of primers.

In one embodiment, the invention is directed to a method of producing a sequencing library, the method comprising the steps of: ligating an adapter oligonucleotide to the 3'-end of a nucleic acid sequence to produce a hybrid sequence comprising a sequence of interest on the nucleic acid sequence and the adapter oligonucleotide, wherein the adapter oligonucleotide comprises: a stem-loop intramolecular nucleotide base pairing; a hydroxyl group at the 3'-end; a phosphate at the 5'-end; a random region complementary to the nucleic acid sequence; and a random region in the loop comprising a molecular barcode; and amplifying the hybrid sequence with a first set of primers.

In some embodiments, the first set of primers comprises a forward universal primer and a reverse universal sample barcoding primer and the reverse universal sample barcoding primer comprises a sample barcode; and amplifying the hybrid sequence with the first set of primers produces a barcoded sequence.

In other embodiments, the first set of primers comprises a target specific primer and a reverse universal primer and amplifying the hybrid sequence with the first set of primers produces a target specific sequence; and the method further comprises amplifying the target specific sequence with a second set of primers comprising a forward universal primer and sample barcoding primer to produce a barcoded sequence.

In one aspect, the reverse universal primer comprises the nucleotide sequence of SEQ ID NO: 2.

In another aspect, the forward universal primer comprises the nucleotide sequence of SEQ ID NO: 1.

In certain aspects, the sample barcoding primer comprises a 5' adapter sequence, a 3' region complementary to the reverse universal primer, and a sample index sequence between the 5' adapter sequence and 3' region complementary to the reverse universal primer.

In one embodiment, the sample barcoding primer comprises the nucleotide sequence of SEQ ID NO: 4.

In yet other embodiments, the method further comprises amplifying the target-specific sequence with a nested target specific primer and the universal primer prior to amplification with the second set of primers.

In certain embodiments, the nucleic acid in the sample is fractionated. In one embodiment, the nucleic acid in the sample is fractionated to fragments between about 100 bp and about 500 bp. In another embodiment, the nucleic acid in the sample is fractionated to fragments between about 250 bp and about 350 bp. In yet another embodiment, the nucleic acid in the sample is fractionated to fragments of about 300 bp.

In some aspects, ligating the adapter oligonucleotide to the 3'-end of the nucleic acid sequence takes place between −20° C. to 40° C. In one aspect, ligating the adapter oligonucleotide to the 3'-end of the nucleic acid sequence takes place between 0° C. and 40° C. In another aspect, ligating the adapter oligonucleotide to the 3'-end of the nucleic acid sequence takes place between 10° C. and 30° C.

In some implementations, the method further comprises cleaning up the amplified sequence with exonuclease and alkaline phosphatase following each amplifying step.

In other implementations, the adapter oligonucleotide is ligated to the 3' end of the nucleic acid sequence with a DNA ligase.

In one aspect, the adapter oligonucleotide further comprises a 3' overhang and the 3' overhang comprises the region complementary to the nucleic acid sequence. In another aspect, the region complementary to the nucleic acid sequence is complementary to the 3'-end of the nucleic acid sequence.

In one embodiment, the stem-loop intramolecular nucleotide base pairing of the adapter oligonucleotide forms a stem of at least 6 nucleotides pairs long. In another embodiment, the stem comprises at least 1 mismatched pair.

In one aspect, the stem-loop intramolecular nucleotide base pairing of the adapter oligonucleotide forms a loop. In another aspect, the loop of the adapter oligonucleotide comprises a primer-binding region for a second universal primer.

In some embodiments, the invention is directed to a sequencing library comprising a nucleic acid sequence tagged with an adapter oligonucleotide at the 3'-end produced with the methods disclosed herein.

In certain aspects, the nucleic acid sequences comprises binding regions for a pair of universal primers and amplification with the pair of universal primers produces an amplicon comprising a sequence of interest for the sequencing library.

Additional objectives, advantages and novel features will be set forth in the description which follows or will become apparent to those skilled in the art upon examination of the drawings and detailed description which follows.

BRIEF DESCRIPTION OF THE DRAWINGS

FIGS. 2A-C depict schematics of the methods of molecular tagging of nucleic acids.

The headings used in the figures should not be interpreted to limit the scope of the claims.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps. Unless specifically noted, it is intended that the words and phrases in the specification and the claims be given their plain, ordinary, and accustomed meaning to those of ordinary skill in the applicable arts.

The term "stem-loop" as used herein in relation to nucleic acid structures refers to a structure formed when two regions of the same strand of nucleic acids can base-pair to form a double helix that ends in an unpaired loop. The two regions of are usually complementary when read in opposite directions. This structure is also known as a hairpin or a hairpin loop.

As used herein, the term "complementary" in reference to nucleic acid sequences refers to nucleic acid base sequences that can form a double-stranded structure by matching base pairs. The degree of complementarity between the sequences does not have to 100%, for example, the degree of complementarity may be at least 95%, at least 90%, or at least 85%.

As used herein, a "nick" in a strand is a break in the phosphodiester bond between two nucleotides in the backbone in one of the strands of a duplex between a sense and an antisense strand.

As used herein, a "gap" in a strand is a break between two nucleotides in the single strand.

The invention relates to methods of molecular tagging nucleic acids, for example, for the preparation of sequencing libraries, and the specially tagged sequencing libraries. As such, the method also related to the special tagged sequence libraries. The sequencing library and methods are particularly useful for informatics analysis of target sequences that are at low fractions in complex mixture of nucleic acid sequences, for example cell-free DNA in biological samples, such as plasma or urine. Another complex mixture of nucleic acid sequences may be low-input degraded forensic sample.

In the context of cancer applications, identification, quantification, and detection of cancer mutations in plasma (with or without knowledge of patient-specific cancer mutations a priori) can be used for screening and early detection of cancer, monitoring treatment response and progression, molecular stratification and assessment of clonal evolution and treatment resistance.

Outside of cancer, such as in non-malignant diseases, this invention enables detection of any genomic variant in circulation or in tissue. In addition, it will enable identification, detection and quantification of variants in any complex mixtures of human or non-human samples such as pathogens. This invention can be scaled for multiplexing such that sequencing of multiple genomic regions is possible using this approach, allowing for simultaneous identification, detection and quantification of multiple mutations. It is also readily customizable and can be implemented on an ad hoc basis or developed to focus on specific scenarios (for example cancer diagnostics using a panel of genes).

Methods of tagging nucleic acid sequences comprise ligation of an adapter oligonucleotide. In some implementation, the nucleic acid sequence in the sample has been fractionated, for example, to fragments between 100 and 500 bp, between 100 and 300 bp, between 250 and 350 bp, or about 300 bp. In some implementations, the methods further comprise a linear amplification step, and in some aspects, the linear amplification step takes place before the ligation step. To prepare a sequencing library, the methods further comprise PCR-based steps (see FIGS. 2A-C). The methods rely on the linear amplification step and/or the PCR-based steps to increase the efficiency of conversion of template molecules into a sequencing-ready library.

1. Linear Amplification.

The linear amplification step comprises annealing a primer to the nucleic acid sequences in the sample and linearly amplifying the nucleic acid sequence. In some implementations, the linear amplification step comprises at least 5 cycles, at least 6 cycles, at least 7 cycles, at least 8 cycles, at least 9 cycles, at least 10 cycles, at least 11 cycles, at least 12 cycles, at least 13 cycles, at least 14 cycles, or at least 15 cycles. In other implementations, the linear amplification step comprises no more than 15 cycles or no more than 10 cycles. For example, the linear amplification step comprises about 10 cycles of amplification.

Figure 2A:
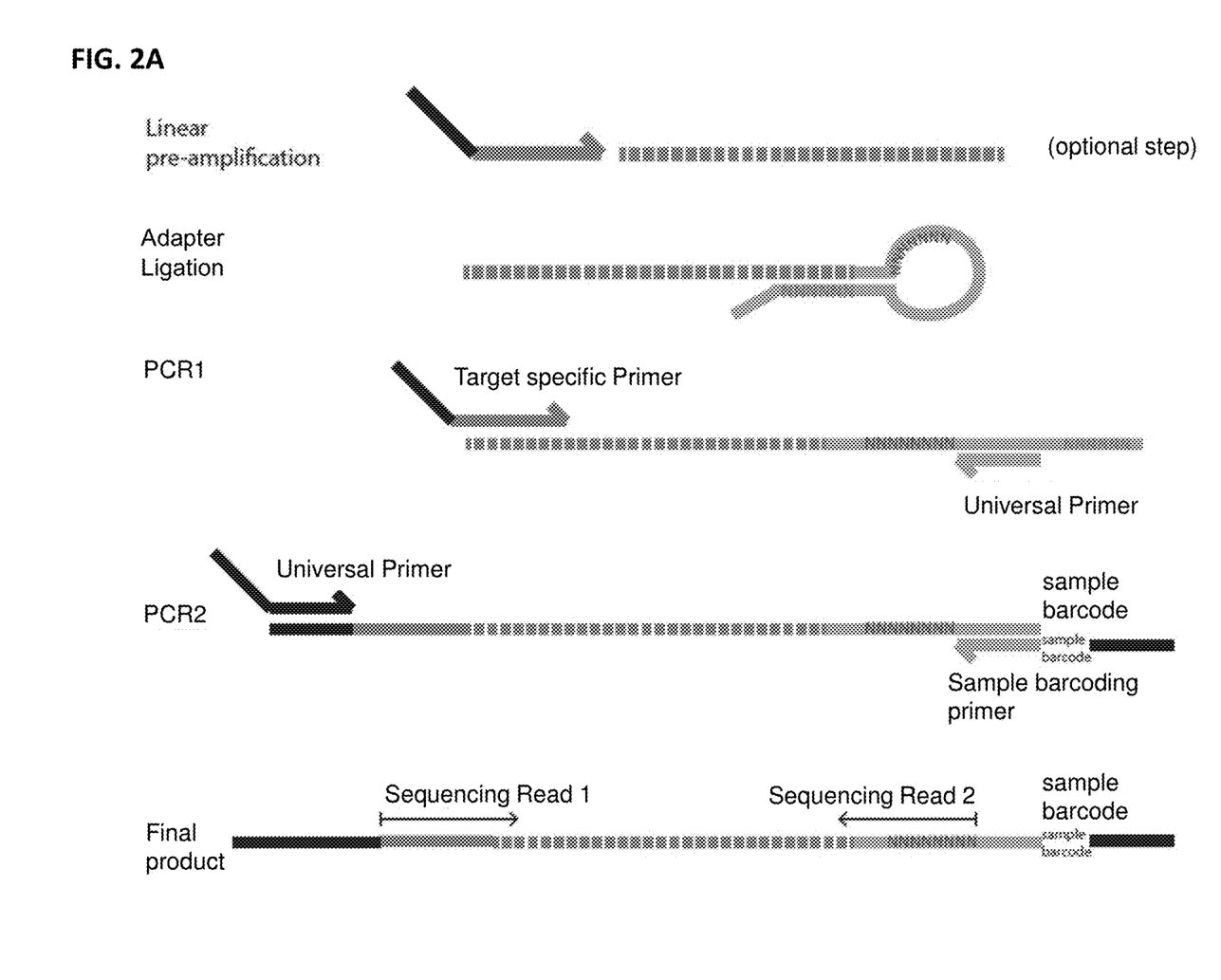
Figure 2B:
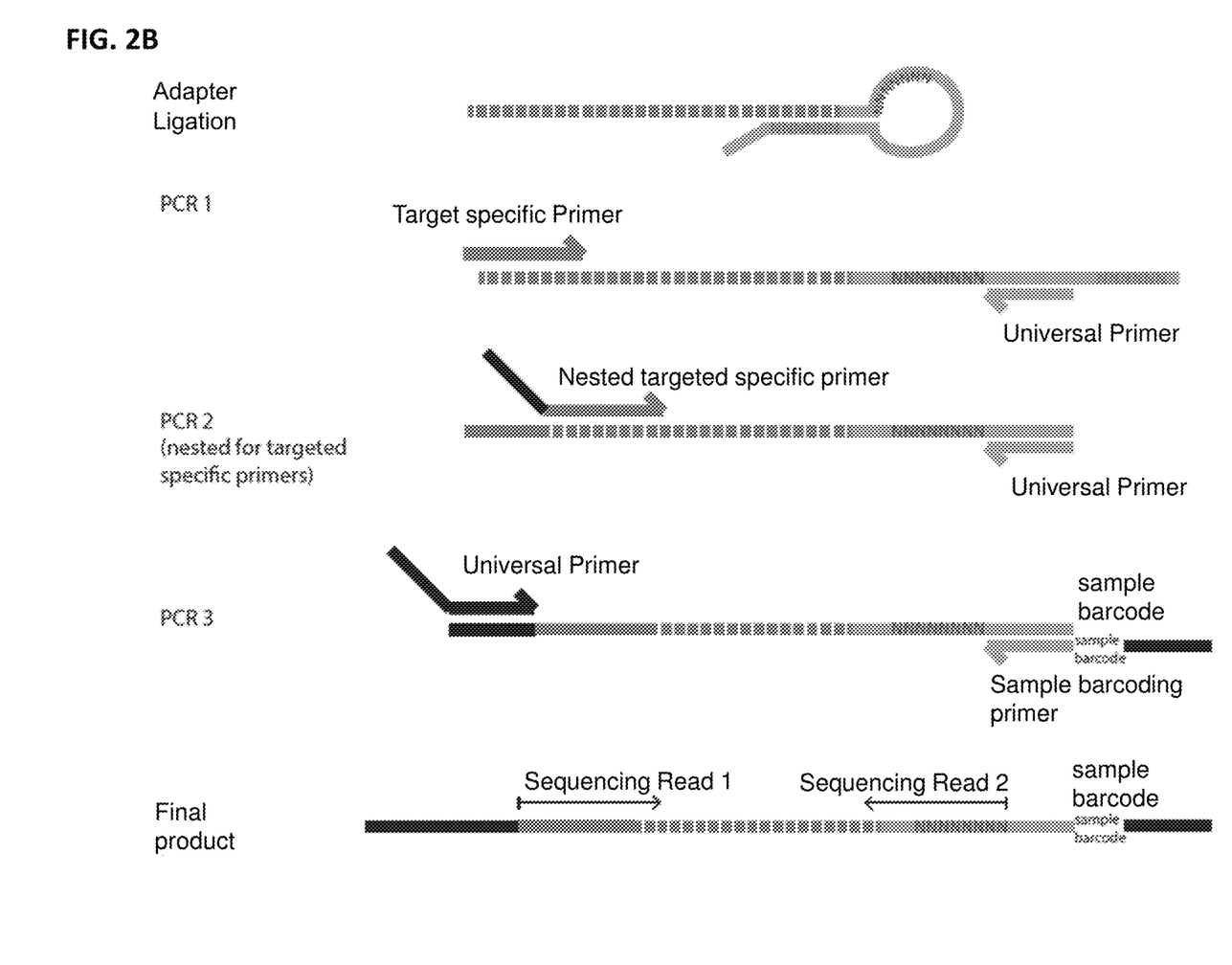
FIG. 2B depicts a variation that utilizes target specific primers as compared to the schematic of FIG. 2A.
Figure 2C:
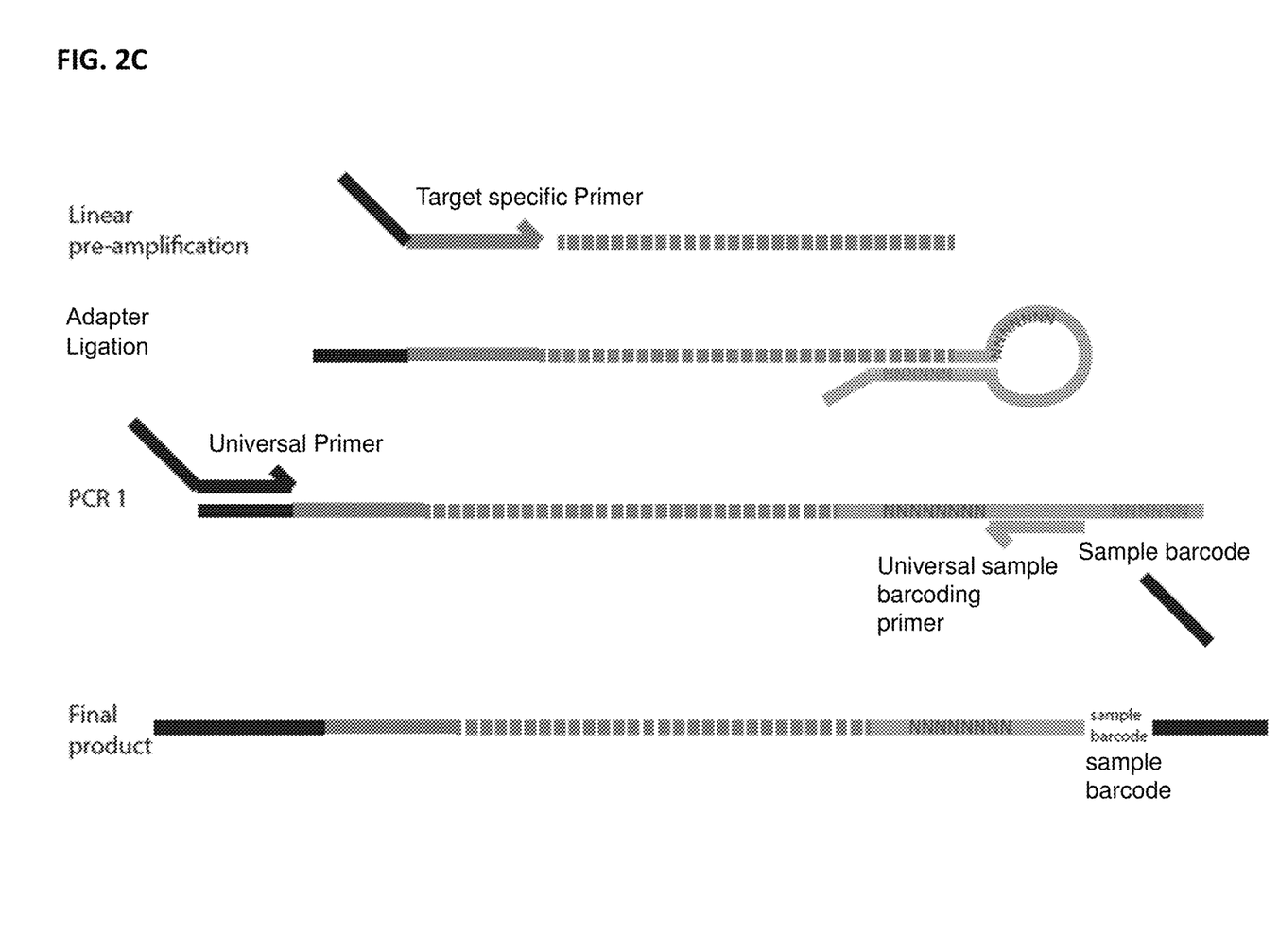
FIG. 2C depicts a variation in how the sample barcode is attached as compared to the schematic of FIG. 2A.
Figure 3:
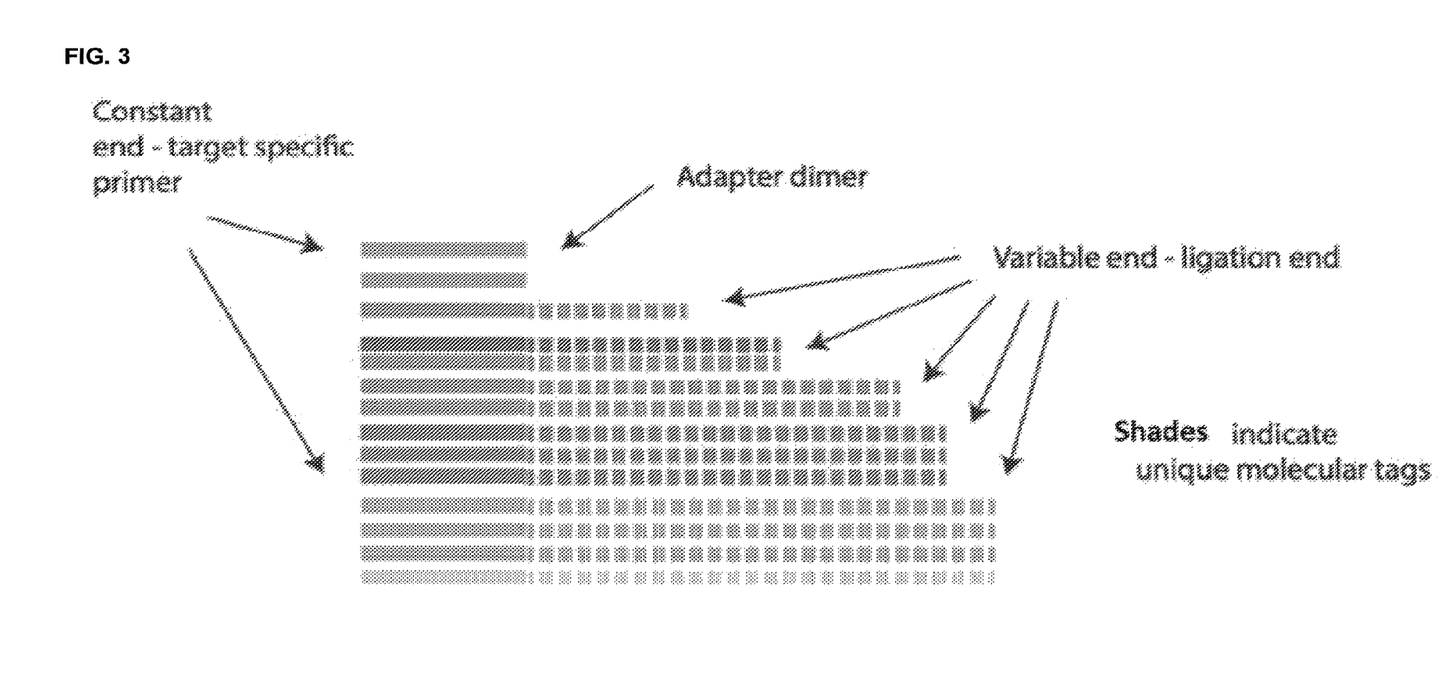
FIG. 3 depicts the expected results of nucleic acid tagging process shown in FIGS. 2A-C.
Figure 4:
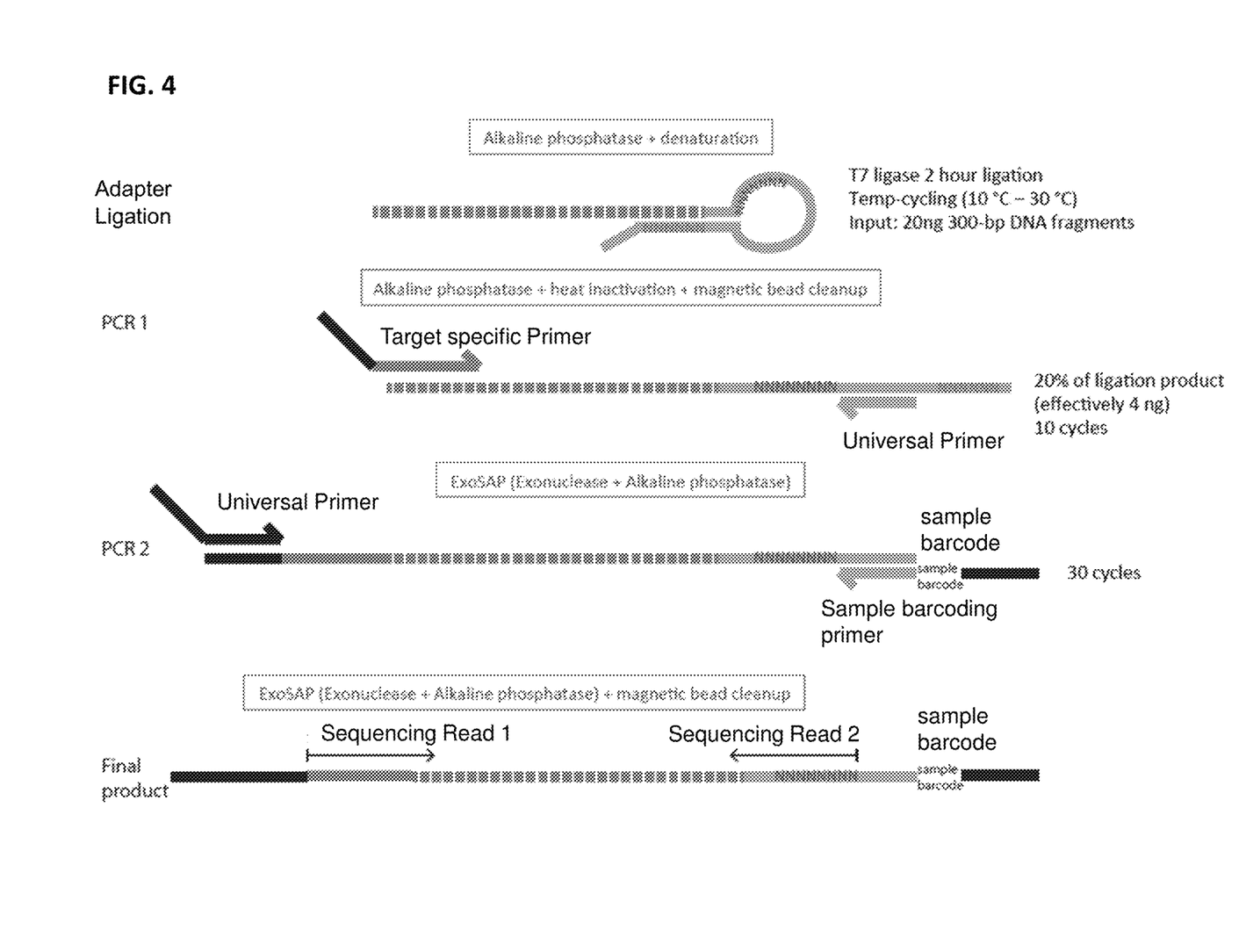
FIG. 4 is a schematic of the steps described in Example A.
Figure 5:
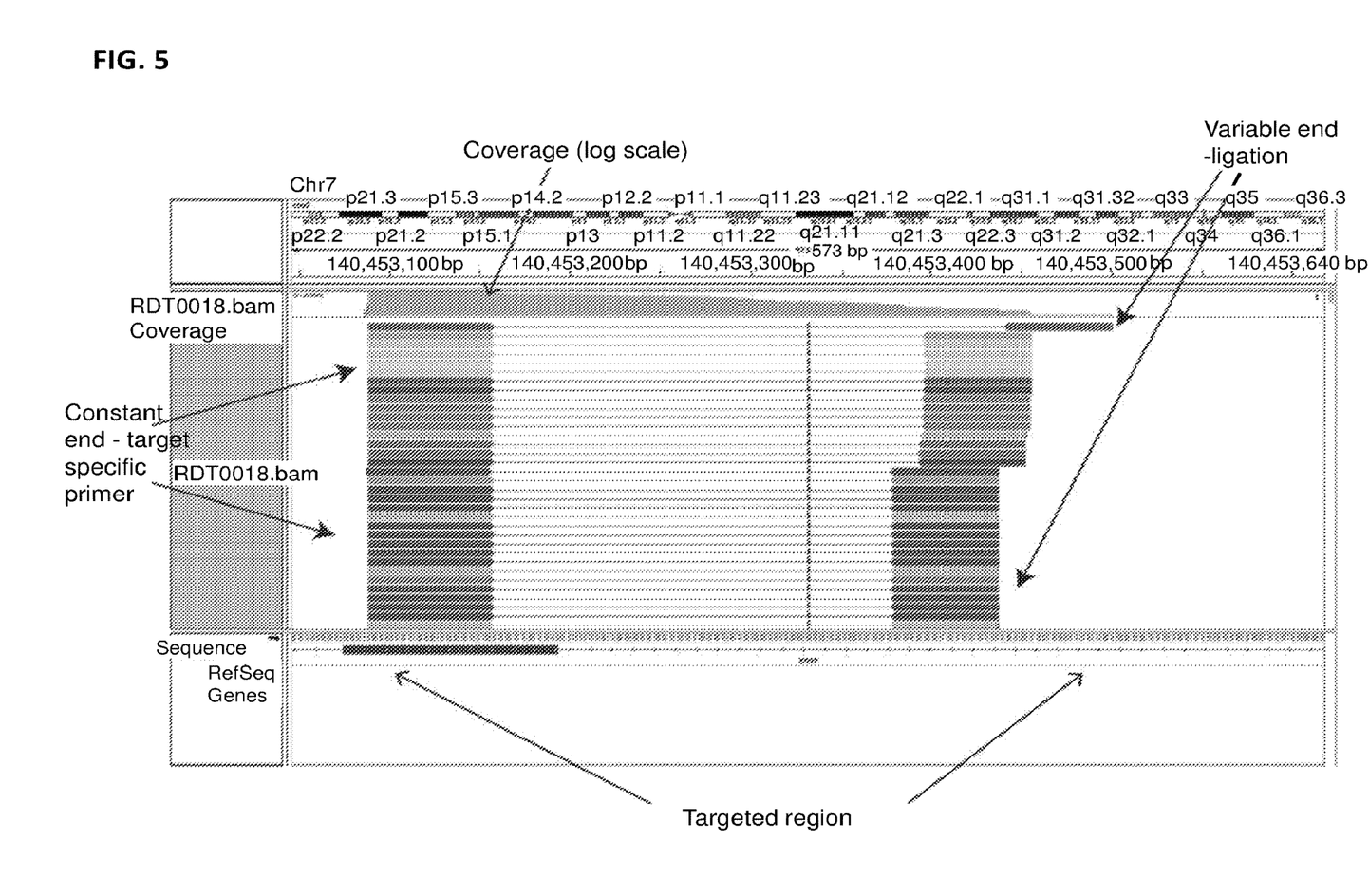
FIG. 5 depicts the observed result from the protocol of Example A.

The primer is complementary to a sequence of interest on the nucleic acid sequence (see PCR1 of FIG. 2A and FIG. 4). For example, sequence of interest on the nucleic acid sequence is a region that is proximal to the region of interest on the nucleic acid sequence.

2. Ligation with adapter oligonucleotide.

The molecular barcode or tag is introduced to the nucleic acid sequences by ligation with an adapter oligonucleotide. The adapter nucleotide is ligated to the 3'-end of the nucleic acid sequence or the 3'-end of the linearly amplified copy of the nucleic acid sequence. In some implementations, the ligation temperature is between −20° C. and 40° C., between 10° C. and 40° C., or between 10° C. and 30° C.

Figure 1:
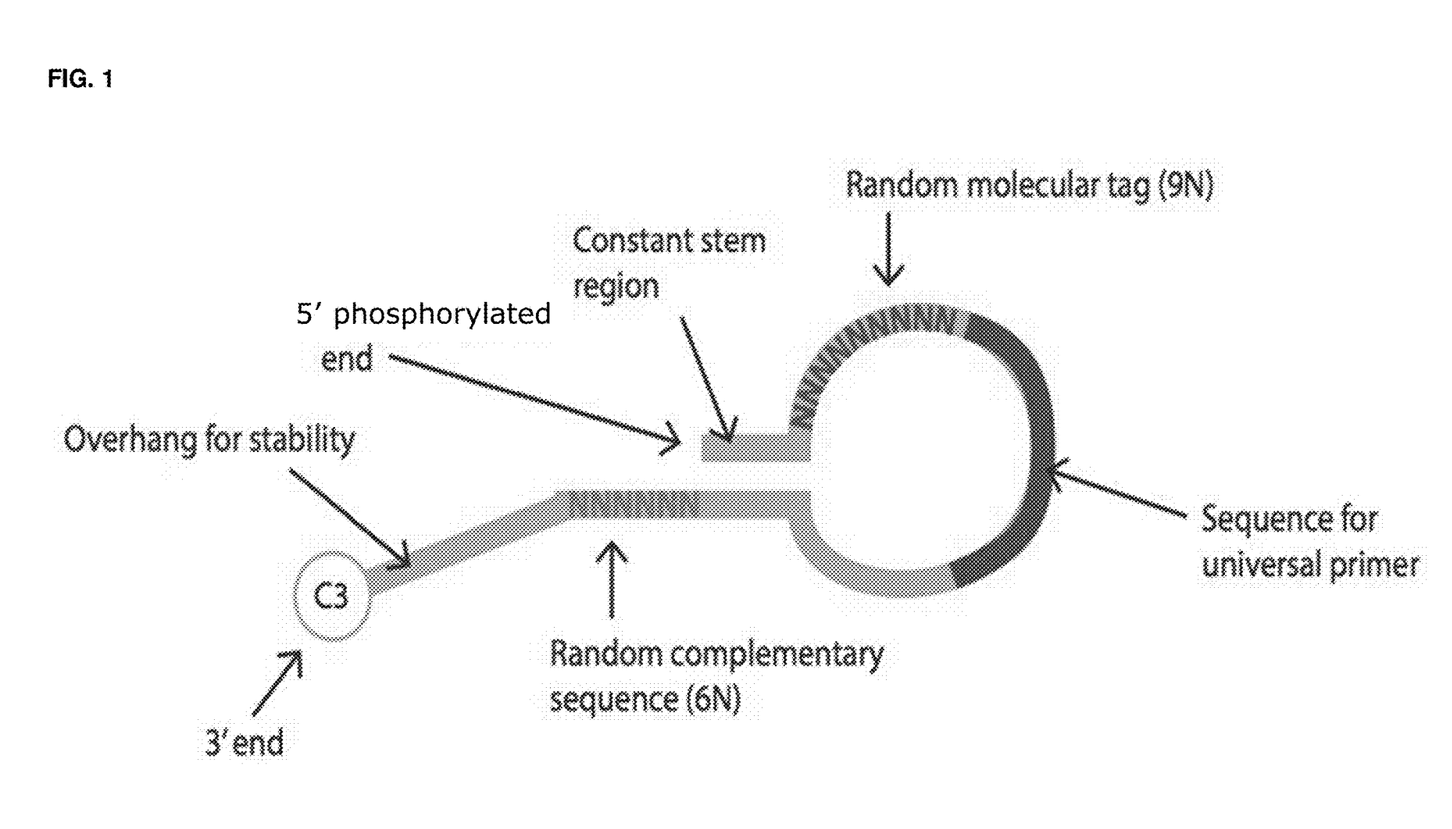
FIG. 1 depicts the generic structure of an exemplary adapter oligonucleotide.

The adapter oligonucleotide comprises a hairpin structure. In preferred embodiments, the adapter oligonucleotide comprises a constant stem region, a random molecule tag, a sequence for a universal primer to bind, and a random complementary sequence. The random molecular tag may be a random oligonucleotide. In some embodiments, the random molecular tag is at least 6 nucleotides long, at least 7 nucleotides long, at least 8 nucleotides long, at least 9 nucleotides long, or at least 10 nucleotides long, while the random complementary sequence is at least 4 nucleotides long, at least 5 nucleotides long, at least 6 nucleotides long, at least 7 nucleotides long, or at least 8 nucleotides long. In other embodiments, the random molecular tag is no more than 9 nucleotides long, no more than 10 nucleotides long, no more than 11 nucleotides long, or no more than 12 nucleotides long, while the random complementary sequence is no more than 6 nucleotides long, no more than 7 nucleotides long, or no more than 8 nucleotides long. In one embodiment, the random molecular tag is 9 nucleotides long while the random complementary sequence is 6 nucleotides long, as shown in FIG. 1.

In some embodiments, the adapter oligonucleotide preferably comprises a phosphate at the 5'-end. In some embodiments, the adapter oligonucleotide comprises a DNA 5'-end and an RNA 3'-end.

To reduce dimerization of the hairpin adapter with itself during ligation, the 3' end of the adapter oligonucleotide may be blocked using an oligonucleotide modification not extendable or cleavable by polymerase, for example a C3 space.

In some aspects, 3' end of the adapter oligonucleotide comprises an overhang after the random complementary sequence for improved stability. In some embodiments, the 3' overhang comprises the region complementary to the nucleic acid sequence. As such, hybridization between the adapter oligonucleotide and the nucleic acid sequence can be ligated either by enzymatic or chemical means. adapter oligonucleotide and the nucleic acid sequence can be ligated either by enzymatic or chemical means.

In one embodiment, the 3'-overhang region comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 20 nucleotides, at least 25 nucleotides, at least 30 nucleotides, at least 35 nucleotides, or at least 40 nucleotides that are complementary to sequences found in the nucleic acid sequence when the nucleic acid sequence and the adapter oligonucleotide are hybridized to one another. In this manner, the 3' overhang region of the adapter oligonucleotide is considered as the region of the adapter oligonucleotide that binds to the 3' region of the nucleic acid sequence.

In various embodiments, the 3'-overhang region comprises at least 1 nucleotide, preferably at least 2 nucleotides, preferably at least 3 nucleotides, preferably at least 4 nucleotides, and preferably at least 5 nucleotides that are mismatched with 25 nucleotides found in the nucleic acid sequence when the nucleic acid sequence and adapter oligonucleotide are hybridized to one another.

In one embodiment, the hybridization between the nucleic acid sequence and the adapter oligonucleotide forms a structure that comprises a nick, wherein the nick can be ligated by either enzymatic or chemical means. In another embodiment, the hybridization between the nucleic acid sequence and the adapter oligonucleotide forms a structure that comprises a gap, wherein the gap can be ligated by either enzymatic or chemical means.

In one embodiment, the hybridization between the nucleic acid sequence and the adapter oligonucleotide forms a stem-loop structure. The stem-loop structure is stable at temperatures as high as 35° C., as high as 40° C., as high as 45° C., as high as 50° C., as high as 55° C., as high as 60° C., as high as 65° C., as high as 70° C., as high as 75° C., as high as 80° C., as high as 85° C., or more. Accordingly, the design of the adapter oligonucleotide should take care to utilizes sequence that ensure the formed stem-loop is thermostable.

The adapter oligonucleotide is a single-stranded oligonucleotide having a double-stranded portion formed of two self-complementary segments, optionally having a loop at one end, and a short overhanging single strand at the other. Thus, for purposes of the present invention, a hairpin is defined as a double-helical region formed by nucleotide base-pairing between adjacent, inverted, at least partially complementary sequences in a single-stranded nucleic acid, preferably within the same single stranded nucleic acid. The stem structure preferably maintains its structure prior to and under conditions suitable for hybridization between the nucleic acid sequence and the adapter oligonucleotide. In this manner, the nick or gap formed through the hybridization between the nucleic acid sequence and the adapter oligonucleotide can be fixed by way of ligation. In some instances, the donor molecule is designed to also have the stem structure be retained under conditions where the nick or gap is ligated by either enzymatic or chemical means. In this situation, a hybrid molecule is created by the ligation between the nucleic acid sequence and the adapter oligonucleotide.

In one embodiment, the intramolecular stem structure preferably maintains the stem structure under conditions suitable for hybridization between the donor and acceptor molecule. For example, the stem structure is designed to maintain its structure under conditions where the acceptor and donor molecule hybridize.

In some conditions, the intramolecular stem structure of the adapter oligonucleotide has reduced stability where the stem structure is unfolded. In this manner, the stem structure can be designed so that the stem structure can be relieved of its intramolecular base pairing and resemble more of a linear molecule. In one embodiment, the adapter oligonucleotide is designed where the relief of the intramolecular stem structure is thermodynamically favored over the intramolecular stem structure. For example, following the ligation of the adapter oligonucleotide and the nucleic acid sequence, some implementations comprise amplifying the ligated nucleic acid product. The stem-loop structure does not impair the amplification step, because the intramolecular stem structure may be undone by raising the temperature or adding a chemical denaturant. Once the intramolecular stem structure is undone, a probe or primer can be used to sequence or amplify at least a portion of the sequence present in the acceptor molecule.

In some embodiments, the stem can comprise at least 3 nucleotide pairs, at least 4 nucleotide pairs, at least 5 nucleotide pairs, at least 6 nucleotide pairs, at least 7 nucleotide pairs, at least 8 nucleotide pairs, at least 9 nucleotide pairs, at least 10 nucleotide pairs, at least 11 nucleotide pairs, at least 12 nucleotide pairs, at least 13 nucleotide pairs, at least 14 nucleotide pairs, at least 15 nucleotide pairs, at least 20 nucleotide pairs, at least 25 nucleotide pairs, at least 30 nucleotide pairs, at least 35 nucleotide pairs, at least 40 nucleotide pairs, at least 45 nucleotide pairs, at least 50 nucleotide pairs, at least 55 nucleotide pairs, at least 60 nucleotide pairs, at least 65 nucleotide pairs, at least 70 nucleotide pairs, at least 75 nucleotide pairs.

In some implementations, the stem region comprises at least 1 mismatched pair, at least 2 mismatched pairs, at least 3 mismatched pairs, at least 4 mismatched pairs, at least 5 mismatched pairs, at least 5 mismatched pairs, at least 6 mismatched pairs, at least 7 mismatched pairs, at least 8 mismatched pairs, at least 9 mismatched pairs, at least 10 mismatched pairs, at least 11 mismatched pairs, at least 12 mismatched pairs, at least 13 mismatched pairs, at least 14 mismatched pairs, at least 15 mismatched pairs, at least 20 mismatched pairs, at least 25 mismatched pairs, at least 30 mismatched pairs, at least 35 mismatched pairs, at least 40 mismatched pairs, at least 45 mismatched pairs, or at least 50 mismatched pairs.

In one embodiment, the amount of mismatch pairs in the stem should be sufficient to make the stem structure unstable at a high temperature of at least 60° C., at least 65° C., at least 70° C., at least 75° C., at least 80° C., at least 85° C., at least 90° C., at least 95° C., at least 96° C., at least 97° C., at least 98° C., or at least 99° C.

The loop structure of the adapter oligonucleotide can comprise any number of nucleotides. In one embodiment, the loop structure comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at 20 least 15 nucleotides, at least 20 nucleotides, at least 25 nucleotides, at least 30 nucleotides, at least 35 nucleotides, or at least 40 nucleotides. Preferably, the loop comprises about 2-30 nucleotides.

In one embodiment, ligation and hybridization is performed using temperature cycling ligation varying in range from −20° C. to 40° C., for example, −20° C. to 4° C., −20° C. to 0° C., 20° C. to 40° C., or 22° C. to 37° C.

3. PCR-Based Steps for Generating a Sequencing Library.

Target-specific and/or universal primers are used to amplify and enrich a nucleic acid sequence of interest. Multiple rounds of PCR are used to achieve adequate enrichment and selection of targeted nucleic acid sequence while minimizing off-target non-specific reads and adapter dimers. In some implementations, the PCR round comprises at least 15 cycles, at least 20 cycles, or at least 25 cycles. In other implementations, the linear amplification step comprises no more than 35 cycles or no more than 30 cycles. For example, the linear amplification step comprises between 20 and 30 amplification cycles, such as 30 cycles. Additional rounds of PCR are used to introduce sample-specific indexes to enable optimum utilization of downstream sequencing. A nested PCR strategy may be used to enrich for on-target reads and reduce off-targeted non-specific amplification and adapter dimers.

In methods for screening a sequence of interest in a genome, the methods further comprise detecting the sequence of interest in the generated sequencing library.

In another aspect, the invention is directed to a sequencing library comprising nucleic acid sequences tagged with an adapter oligonucleotide and regions that are binding sites for a pair of universal primers.

It is well established in the art that, when performing different types of reactions with nucleic acids, for example a PCR after a ligation reaction, it is sometimes necessary to clean up the sample after each reaction before proceeding to the next. As shown in FIG. 4, the addition of alkaline phosphatase ensures a more efficient ligation reaction. Heat inactivation also ensure the complete end of the ligation reaction. Methods for cleaning up a PCR product are well established in the field, and an example is the use of a combination of exonuclease and alkaline phosphatase.

EXAMPLES

It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Example A: Protocol for Generation of Molecular Barcoded Sequencing Library

1. Sample from sheared DNA D6 (2 replicate samples and 1 blanks for EXP266b and same for EXP266c). D6 at 10 ng/µl (sheared previously using sonication to ~300 bp fragments). The contents of each test tube are reflected in Table 1.

TABLE 1

| Tube | Input | Sample volume (µl) | Water (µl) | Volume before AP (µl) | AP + buffer* | Sample |
|---|---|---|---|---|---|---|
| 1 | 2 | 2 | 5 | 7.0 | 1 + 1 | #D6 |
| 2 | 2 | 2 | 5 | 7.0 | 1 + 1 | #D6 |
| 3 | — | 0 | 7 | 7.0 | 1 + 1 | #blank |

*Added FASTAP buffer and enzyme making a 6.6 µl (3.3 and 3.3 each) master mix.

2. Denature DNA by incubation in 37° C. for 10 minutes and then in 95° C. for 3 minutes. Immediately after the end of incubation at 95° C., incubate in an ice water bath. While in the ice water bath, add the oligo (0.5 µl from 100 µM stock) and the master mix (11 µl from recipe described in Table 2) to each tube.

TABLE 2

| Reagents | 20 µl reaction | Per reaction | mm 3x (+10%) |
|---|---|---|---|
| 2X T7 DNA ligase buffer | 1x | 10 | 33 |
| T7 DNA ligase | 5U | 1 | 3.3 |
| | | 20 | |

3. Ligate ssDNA by incubation in 40 cycles of 10° C. for one minute and 30° C. for one minute. This ligation product may be stored in 4° C. until the next step.

4. Add FastAP and incubate at 37° C. for 30 minutes. The amount of AP and buffer added for teach tube is depicted in Table 3.

TABLE 3

| Tube | Volume before AP (µl) | AP + buffer | Sample |
|---|---|---|---|
| 1 | 7.0 | 1 + 1 | #D6 |
| 2 | 7.0 | 1 + 1 | #D6 |
| 3 | 7.0 | 1 + 1 | #blank |

Added FASTAP buffer and enzyme making a 13.5 µl (6.7 and 6.7 each) master mix.

5. Magnetic beads are used to clean up the ligation reaction (1.8 ratio of beads to DNA by volume). The total reaction of the cleanup reaction per tube is 25 µl. The specific steps for clean up with magnetic beads are as follows:

a. Prepare fresh 85% ethanol–850 µl of 100% ethanol+ 150 µl of water (if needed)–will need total of 360 µl×4 reactions=1440~2 mLs or 2×1 mL preps.

b. Add 45 µl of well-resuspended magnetic beads and pipette mix well.

c. Incubate DNA and beads for 5 minutes at room temperature.

d. Place beads+DNA on the magnetic and wait until all beads are collected and supernatant is clear.

e. Remove supernatant carefully (do not remove beads).

f. While on the magnetic, Wash 2× with 85% ethanol by adding 180 ul of 85% ethanol, wait 30 s and aspirate g. Tap the magnetic to collect all ethanol at the bottom of the tubes and remove any leftover ethanol Let it dry at RT for no longer than 5 minutes.

h. Add 20 µl of water and mix well with pipette.

i. Incubate for 2 minutes at room temperature.

j. Place tubes back on the magnetic for a few minutes until all beads are collected. And transfer the cleaned product to a new set of tubes (or a new strip tube). Recover ~17.0 µl per reaction.

6. The first PCR (named PCR1 in FIG. 4) is performed using the primers depicted in Table 4. The master mix for the PCR reaction is prepared according to Table 5. Table 6 describes the cycling conditions for the first PCR.

TABLE 4

| | |
|---|---|
| MB_BRAF_v600_F<br>Forward target-specific primer | 5'-<u>CGC TCT TCC GAT CTC TGA TCC AGA CAA CTG TTC</u> AAA CTG A-3' (SEQ ID NO: 1)<br>Underlined: universal 5' overhang to introduce adapter<br>Non-underlined: target specific primer<br>On BLAST (program for comparing primary biological sequence information), primer perfectly aligns with another region on chromosome X besides BRAF on chr 7. |
| universalReverse1<br>Reverse universal primer | 5'-GTGACTGGAGTTCAGACGTGTGCTCTTCCGATCTGAC-3'<br>(SEQ ID NO: 2) |
| Ligation Oligo #2<br>Hairpin adapter | /5Phos/TGC TCT TTG (N1:25252525)(N1)(N1)(N1)(N1)(N1)(N1)(N1)(N1) GTC AGA TCG GAA GAG CA(N1)(N1)(N1)(N1)(N1)(N1)C TGC CCA TAG AG/3SpC3/ (SEQ ID NO: 3)<br>intended extra length: 9 + 8 = 17 bp |

TABLE 5

| MM #1 | Units | Starting conc. | Final conc. | Vol (µl) per rxn |
|---|---|---|---|---|
| KAPA™ Fast Probe Master Mix | X | 2 | 1 | 5.0 |
| MB_BRAF_v600_F | µM | 10 | 0.6 | 0.6 |
| universal Reverse1 | µM | 10 | 0.6 | 0.6 |
| Water | µM | | | 0.13 |
| Ligation product | ng | | | 3.7 |

TABLE 6

| Temp (° C.) | Cycle time | # of cycles |
|---|---|---|
| 95 | 2 min | 1 |
| 95 | 15 sec | 10 |
| 60 | 20 sec | |
| 72 | 15 sec | |
| 4 | | hold |

7. ExoSAP clean up is performed using 10 µl of PCR production and 4 µl ExoSAP-IT for 1 replicate of each of the above. ExoSAP incubation was setup per manufacturer's instructions, which is incubation at 37° C. for 30 minutes followed by incubation at 85° C. for 15 minutes.

8. The second PCR reaction (named PCR2 in FIG. 4) is performed using the primers depicted in Table 7. The contents of each PCR reaction is described Table 8. Table 9 describes the cycling conditions for the first PCR.

TABLE 7

| | |
|---|---|
| F_universal<br>(universal sequences were based on the RAINDANCE™ targeted sequencing protocol due to ease of reach - the protocol does not rely on these sequences and can switch them without consequence) | 5'-<u>CGC TCT TCC GAT CTC TGA TCC AGA CAA CTG TTC</u> AAA CTG A-3' (SEQ ID NO: 1) |
| R-Barcode<br>Sample barcoding primer (based on the RAINDANCE™ structure and protocol but can be switched to ILLUMINA® standard sequences). | 5'-CAAGCAGAAGACGGCATACGAGAT*CGTGAT*GTGACT GGAGTTCA GACGTGTGCTCTTCCGATCTGAC-3' (SEQ ID NO: 4)<br>Underlined: same as universalReverse1<br>Bold italic: sample index introduced [as an example, changed for every sample]<br>Regular: additional adapter sequence (PE7 compatible for ILLUMINA® sequencing) |

TABLE 8

| MM #1 | Vol (μl) per rxn | Total μl |
|---|---|---|
| KAPA ™ | 12.5 | 12.5 |
| F-Universal | 1.25 | 1.25 |
| R-Barcode | 1.25 | 1.25 |
| PCR1 product | 10 | 10 |

TABLE 9

| Temp (° C.) | Cycle time | # of cycles |
|---|---|---|
| 95 | 2 min | 1 |
| 95 | 15 sec | 30 |
| 60 | 20 sec | |
| 72 | 15 sec | |
| 4 | | hold |

9. Another ExoSAP clean up is performed. This time 25 μl of PCR production and 10 μl ExoSAP-IT is used per reaction. ExoSAP incubation was setup per manufacturer's instructions, which is incubation at 37° C. for 30 minutes followed by incubation at 85° C. for 15 minutes. The products of the cleanup may be stored in 4° C. until the next step is performed.

10. Magnetic beads are used to clean up the PCR products (1.2 ratio of beads to DNA by volume). The specific process is the same those described in step 5 but with the amount of beads adjusted. The elution step is adjusted to 16 μl where about 13 μl per reaction.

11. Kappa Library quantification using qPCR is performed according to the manufacturer's protocol.

12. Quality control of the library is performed using the bioanalyzer.

13. The library is sequenced using MiSeq. All samples are put at 4 nM. The pool contains 4 nM of each sample included for MiSeq with a volume 10 μl per sample. For the blank sample, 1 μl was placed in the pool.

Example B: Summary Table

TABLE 10

| | 265b | 265c |
|---|---|---|
| Ligation Alkaline phosphatase | ✓ | ✓ |
| Denaturation | ✓ | ✓ |
| Ligation | ✓ | ✓ |
| Alkaline phosphatase | ✓ | ✓ |
| Magnetic bead cleanup (1.8x) | ✓ | ✓ |
| Heat inactivation (85° C., 15 min) | ✓ | ✓ |
| PCR1 (10 cycles) | 60° C. annealing; BRAF primer | 60° C. annealing; BRAF primer |
| Exosap (exonuclease + alkaline phosphatase) | ✓ | ✓ |
| PCR2 (30 cycles) | | |
| Exosap | ✓ | ✓ |
| Magnetic bead clean up (1.2x) | ✓ | ✓ |
| Kappa library quantification | ✓ | ✓ |
| Bioanalyzer | ✓ | ✓ |
| MiSeq | ✓ | ✓ |

---

What is claimed is:

1. A method of producing a sequencing library from a nucleic acid sample, the method comprising the steps of:
   annealing target-specific linear pre-amplification primers to nucleic acids, comprising a nucleic acid sequence of interest, in the nucleic acid sample and producing single-stranded nucleic acids by repeating at least 5 cycles of linear amplification;
   ligating an adapter oligonucleotide to the 3'-end of the single-stranded nucleic acids in the nucleic acid sample to produce hybrid nucleic acids comprising the nucleic acid sequence of interest and the adapter oligonucleotide, wherein the adapter oligonucleotide comprises:
   a stem-loop intramolecular nucleotide base pairing forming a loop;
   a hydroxyl group at the 3'-end;
   a phosphate at the 5'-end;
   a 3' overhang comprising a first random region complementary to the nucleic acid sequence of interest;
   a second random region in the loop comprising a molecular barcode, and
   a universal primer-binding region positioned in the loop and 3' to the second random region in the loop comprising a molecular barcode;
   wherein the first random region complementary to the nucleic acid sequence of interest in the adapter oligonucleotide hybridizes to the nucleic acid sequence of interest; and
   amplifying the hybrid nucleic acids by polymerase chain reaction (PCR) with a first set of PCR primers.

2. The method of claim 1, wherein the first set of PCR primers comprise target specific primers and a reverse universal primer and the PCR amplification step provides amplified target-specific sequences; and
   wherein the method further comprises amplifying the amplified target-specific sequences with a second set of PCR primers comprising a forward universal primer and sample barcoding primer to provide amplified barcoded target-specific sequences.

3. The method of claim 2, wherein the reverse universal primer comprises the nucleotide sequence of SEQ ID NO: 2, and the forward universal primer comprises the nucleotide sequence of SEQ ID NO: 1.

4. The method of claim 2, wherein the sample barcoding primer comprises a 5' adapter sequence, a 3' region comprising the reverse universal primer, and a sample index sequence between the 5' adapter sequence and the 3' region comprising the reverse universal primer.

5. The method of claim 4, wherein the sample barcoding primer comprises the nucleotide sequence of SEQ ID NO: 4.

6. The method of claim 2, further comprising amplifying the amplified target-specific sequences with nested target-specific primers and the reverse universal primer prior to amplification with the second set of PCR primers.

7. The method of claim 1, wherein the nucleic acids in the sample are fractionated.

8. The method of claim 1, wherein ligating the adapter oligonucleotide to the 3'-end of the nucleic acids takes place between −20° C. to 40° C.

9. The method of claim 1, further comprising treating the PCR amplified nucleic acids with exonuclease and alkaline phosphatase following the PCR amplification step.

10. The method of claim 1, wherein the adapter oligonucleotide is ligated to the 3' end of the nucleic acids with a DNA ligase.

11. The method of claim 1, wherein the stem-loop intramolecular nucleotide base pairing of the adapter oligonucleotide forms a stem of at least 6 nucleotide pairs long.

12. The method of claim 11, wherein the stem comprises at least 1 mismatched pair.

13. The method of claim 1, wherein the 3' overhang further comprises a stabilizing region that does not hybridize to the nucleic acid of interest and that is 3' to the first random region.

14. A method of producing a sequencing library from a nucleic acid sample comprising single-stranded nucleic acids having 3'-ends and a sequence of interest, the method comprising the steps of:
   ligating an adapter oligonucleotide to the 3'-end of the single-stranded nucleic acids in the nucleic acid sample to produce hybrid nucleic acids comprising the nucleic acid sequence of interest and the adapter oligonucleotide, wherein the adapter oligonucleotide comprises:
   a stem-loop intramolecular nucleotide base pairing forming a loop;
   a hydroxyl group at the 3'-end, the 3' end providing an overhang region comprising a first random region that hybridizes to the single-stranded nucleic acids and a stabilizing region that does not hybridize to the single-stranded nucleic acids and that is 3' to the first random region;
   a phosphate at the 5'-end;

a second random region in the loop comprising a molecular barcode, and a universal primer-binding region positioned in the loop and 3' to the second random region in the loop comprising a molecular barcode; and amplifying the hybrid nucleic acids by polymerase chain reaction (PCR) with a first set of PCR primers.

15. The method of claim 14, wherein the first set of PCR primers comprise target specific primers and a reverse universal primer and the PCR amplification step provides amplified target-specific sequences; and wherein the method further comprises amplifying the amplified target-specific sequences with a second set of PCR primers comprising a forward universal primer and sample barcoding primer to provide amplified barcoded target-specific sequences.

16. The method of claim 15, wherein the sample barcoding primer comprises a 5' adapter sequence, a 3' region comprising the reverse universal primer, and a sample index sequence between the 5' adapter sequence and the 3' region comprising the reverse universal primer.

17. The method of claim 15, further comprising amplifying the amplified target-specific sequences with nested target-specific primers and the reverse universal primer prior to amplification with the second set of PCR primers.

18. The method of claim 14, wherein the nucleic acids in the sample are fractionated.

19. The method of claim 14, wherein ligating the adapter oligonucleotide to the 3'-end of the nucleic acids takes place between −20° C. to 40° C.

20. The method of claim 14, wherein the adapter oligonucleotide is ligated to the 3' end of the nucleic acids with a DNA ligase.

21. The method of claim 14, wherein the stem-loop intramolecular nucleotide base pairing of the adapter oligonucleotide forms a stem of at least 6 nucleotide pairs long.

* * * * *

SEQUENCE LISTING

<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
cgctcttccg atctctgatc cagacaactg ttcaaactga                40

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
gtgactggag ttcagacgtg tgctcttccg atctgac                   37

<210> SEQ ID NO 3
<211> LENGTH: 53
<212> TYPE: DNA
<213> ORGANISM: Artificial Sequence
<220> FEATURE:
<223> OTHER INFORMATION: Hairpin adapter
<220> FEATURE:
<221> NAME/KEY: misc_feature
<222> LOCATION: (10)..(18)
<223> OTHER INFORMATION: n is any nucleotide
<220> FEATURE:
<221> NAME/KEY: misc_feature

```
<222> LOCATION: (36)..(41)
<223> OTHER INFORMATION: n is any nucleotide

<400> SEQUENCE: 3
tgctctttgn nnnnnnnngt cagatcggaa gagcannnnn nctgcccata gag         53

<210> SEQ ID NO 4
<211> LENGTH: 67
<212> TYPE: DNA
<213> ORGANISM: Artificial Sequence
<220> FEATURE:
<223> OTHER INFORMATION: barcode primer

<400> SEQUENCE: 4
caagcagaag acggcatacg agatcgtgat gtgactggag ttcagacgtg tgctcttccg    60
atctgac                                                              67
```